United States Patent [19]

Grey et al.

[11] Patent Number: 5,401,856
[45] Date of Patent: Mar. 28, 1995

[54] PROCESS FOR MAKING PYRROLIDONES

[75] Inventors: Roger A. Grey, West Chester; Diandre Armstead, Philadelphia, both of Pa.

[73] Assignee: ARCO Chrmical Technology, L.P., Greenville, Del.

[21] Appl. No.: 202,519

[22] Filed: Feb. 28, 1994

[51] Int. Cl.6 .................................... C07D 207/263
[52] U.S. Cl. ............................ 548/552; 546/257; 546/287; 546/288; 546/304; 546/332; 546/348; 546/88
[58] Field of Search ................................ 548/552

[56] References Cited

U.S. PATENT DOCUMENTS

| | | | |
|---|---|---|---|
| 3,637,743 | 1/1972 | Prince | 260/326.5 |
| 3,714,185 | 1/1973 | McCoy et al. | 260/326.5 |
| 4,110,340 | 8/1978 | Knifton | 260/326.5 |
| 4,111,952 | 9/1978 | Knifton | 260/326.5 |

OTHER PUBLICATIONS

Tetrahedron Lett. (1965) 2677.
Chem. Ber. 98 (1965) 1228.
Ang. Chem., Int., Ed. Eng 5, (1966) 435.
J. Organometal. Chem., 188, (1980) 223.
Alper et al. J. Org. Chem., 57, (1992) 3328.

*Primary Examiner*—David B. Springer
*Attorney, Agent, or Firm*—Jonathan L. Schuchardt

[57] ABSTRACT

A cyclocarbonylation process for making pyrrolidones under mild temperature and pressure conditions is disclosed. In the process, an allylic amine reacts with carbon monoxide in the presence of a rhodium carbonyl catalyst and an amount of a pyridine promoter effective to enhance the yield of pyrrolidone obtained in the process compared with the yield obtained in the absence of the promoter. The process can be used to make N-methyl-2-pyrrolidone from N-methylallylamine.

18 Claims, No Drawings

PROCESS FOR MAKING PYRROLIDONES

FIELD OF THE INVENTION

The invention relates to a process for making pyrrolidones. In particular, the invention is a process for making pyrrolidones by reacting an allylic amine with carbon monoxide in the presence of a rhodium carbonyl catalyst and a pyridine promoter.

BACKGROUND OF THE INVENTION

Pyrrolidones are useful organic solvents and chemical intermediates. N-methyl-2-pyrrolidone, for example, is widely used in cleaners and coating removers, and is a less toxic alternative to halogenated hydrocarbons such as methylene chloride. In one commercial process, N-methyl-2-pyrrolidone is produced in a multi-step process from allyl alcohol. Hydroformylation of allyl alcohol gives 4-hydroxybutanal, which is dehydrogenated to $\gamma$,-butyrolactone, which is then reacted with methylamine to give N-methyl-2-pyrrolidone. A potentially more attractive route converts N-methylallylamine directly to N-methyl-2-pyrrolidone in a cyclocarbonylation process:

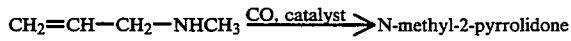

Cyclocarbonylation of allylic amines to pyrrolidones using cobalt carbonyl catalysts is described by Falbe and coworkers (*Tetrahedron Lett.* (1965) 2677; *Chem. Ber.* 98 (1965) 1228; *Ang. Chem. I.E. Eng.* 5 (1966) 435). The reaction requires high temperatures (230°–280° C.) and pressures (300 atmospheres), and gives pyridine by-products under some conditions.

McCoy et al. (U.S. Pat. No. 3,714,185) teach phosphine complexes of cobalt and rhodium as catalysts for making 2-pyrrolidone from allyl amine. The phosphine catalysts permit preparation of the pyrrolidones at lower temperatures and pressures than those reported earlier.

Knifton (U.S. Pat. No. 4,111,952; *J. Organometal. Chem.* 188 (1980) 223) teaches to use rhodium catalysts to prepare pyrrolidones from allyl halides or allylic amines. Pressures of at least about 10 atmospheres are required for substantial conversion of the allylic amine to the pyrrolidone products.

Improved cyclocarbonylation processes are needed. An ideal process would allow short reaction times and would result in high conversions of allylic amines with good selectivity to pyrrolidones at relatively mild temperatures and low pressures. Preferably, the pyrrolidone would be the only carbonylation product.

SUMMARY OF THE INVENTION

The invention is a process for making pyrrolidones. The process comprises reacting an allylic amine with carbon monoxide in the presence of a rhodium carbonyl catalyst and a pyridine promoter to produce the pyrrolidone. We surprisingly found that using a pyridine promoter with a rhodium carbonyl catalyst markedly improves conversion of allylic amines to pyrrolidones and consequently gives enhanced yields of the pyrrolidones. Pyrrolidones are the only carbonylation products. The by-products from the process include structural isomers of the allylic amine, which can be converted back to the allylic amine and recycled to the cyclocarbonylation process. The cyclocarbonylation process of the invention proceeds smoothly at relatively mild temperatures and low pressures.

DETAILED DESCRIPTION OF THE INVENTION

In the process of the invention, an allylic amine reacts with carbon monoxide in the presence of a rhodium carbonyl catalyst and a pyridine promoter to give a pyrrolidone.

An allylic amine is used in the process of the invention. Preferred allylic amines have the structure:

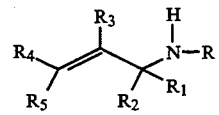

in which each of R, $R_1$, $R_2$, $R_3$, $R_4$, and $R_5$ separately represents hydrogen or a linear, branched, or cyclic $C_1$–$C_{16}$ alkyl, aryl, or aralkyl group. In the formula, at least one of $R_1$ and $R_2$ is hydrogen, and at least one of $R_4$ and $R_5$ is hydrogen. Suitable allylic amines include, for example, allyl amine, N-methylallylamine, methallylamine, 3-buten-2-amine, 3-methyl-3-penten-2-amine, 2-methyl-2-propen-1-(N-methylamine), 3-phenyl-3-buten-2-amine, and the like, and mixtures thereof. Allyl amine and N-methyl-allylamine are particularly preferred.

A pyrrolidone is produced in the process of the invention. Preferred pyrrolidones will have the structure:

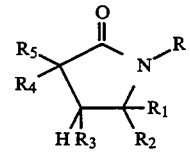

in which R, $R_1$, $R_2$, $R_3$, $R_4$, and $R_5$ are as described above for the allylic amines. Thus, pyrrolidones available from the process of the invention include, for example, 2-pyrrolidone, N-methyl-2-pyrrolidone, N-phenyl-2-pyrrolidone, 3,4,5-trimethyl-2-pyrrolidone, 4-methyl-2-pyrrolidone, 5-phenyl-2-pyrrolidone, and the like. Particularly preferred are 2-pyrrolidone and N-methyl-2-pyrrolidone.

By "rhodium carbonyl catalyst," we mean a rhodium carbonyl compound or a rhodium compound that converts to a rhodium carbonyl compound in the presence of carbon monoxide. Preferred catalysts include rhodium carbonyls; rhodium compounds and rhodium carbonyl compounds that contain complexed ligands such as halides, nitrates, carboxylates, sulfonates, and amines; elemental forms of rhodium; rhodium compounds that contain complexed olefins; and polymer-bound rhodium.

Suitable catalysts include, for example, hexarhodium hexadecacarbonyl, tetrarhodium dodecacarbonyl, chlorodicarbonylrhodium (I) dimer, chloronorbonadiene rhodium (I) dimer, chloropentaaminerhodium (III) chloride, dicarbonylacetylacetonato rhodium (I), rhodium (II) acetate dimer, rhodium on alumina, rhodium on carbon, rhodium on silica, bis(1,5-cyclooctadiene)rhodium (I) triflate, chlorobis(ethylene)-rhodium (I) dimer, chloro(1,5-cyclooctadiene)rhodium (I) dimer, rhodium (III) acetylacetonate, rhodium (III) bromide, rhodium (III) chloride, rhodium (III) nitrate, rhodium (II) octanoate dimer, tris(ethylenediamine)rhodium (III) chloride, bis[(pentamethylcyclopentadienyl)dichlororhodium], polyvinylpyridine-bound rhodium, and the like.

The amount of rhodium carbonyl catalyst used depends on many factors, including the allylic amine used, the particular catalyst type, the desired reaction rate, and so on. Generally, the rhodium carbonyl catalyst will be used in an amount within the range of about $10^{-6}$ to about $10^{-1}$ moles (as rhodium) per mole of allylic amine used. A more preferred range is from about $10^{-5}$ to about $10^{-2}$ moles Rh per mole of allylic amine.

A pyridine promoter is used in the process of the invention. The promoter is pyridine or a compound having a pyridine moiety. Suitable pyridine promoters include, but are not limited to, pyridine, (dialkylamino)pyridines, alkylpyridines, arylpyridines, ortho-bipyridines, cyanopyridines, (2-hydroxyethyl)pyridines, phenanthrolines, (pyrrolidino)pyridines, and the like. Specific examples include pyridine, 4-(dimethylamino)pyridine, 3-methylpyridine, 4-ethylpyridine, 4cyanopyridine, 4-(2-hydroxyethyl)pyridine, 3-phenylpyridine, phenanthroline, 2,2'-bipyridine, and the like. Mixtures of pyridine promoters can be used. Pyridine and (dialkylamino)pyridines are preferred.

The amount of pyridine promoter used is not critical. The required amount of promoter is an amount effective to enhance the yield of the pyrrolidone compared with the yield obtained in the absence of the promoter. Generally, it is preferred to use at least about 0.1 mole of the pyridine promoter per mole of allylic amine used. If desired, however, the pyridine promoter can even be used as a solvent (e.g., as much as 100 moles of pyridine promoter per mole of allylic amine). A preferred range is from about 0.5 moles to about 2 moles of pyridine promoter per mole of allylic amine. Most preferred is the range from about 1 to about 2 moles.

An organic solvent is optionally used in the process of the invention. Suitable organic solvents are compounds that do not react with the amine promoter, the allylic amine, or the pyrrolidone under the reaction conditions. Suitable solvents include, for example, aliphatic and aromatic hydrocarbons, halogenated hydrocarbons, ethers, alcohols, nitriles, and the like, and mixtures thereof.

The reaction is performed under an atmosphere of carbon monoxide. If desired, up to about 50 mole percent of hydrogen can be included with the CO, but hydrogen is not necessary. Preferably, the amount of hydrogen present is less than about 5 mole percent. When more than about 50 mole percent of hydrogen is used, the process gives an undesirable amount of hydroformylation products.

Unlike other cyclocarbonylation processes known in the art, the process of the invention can be performed at relatively low gas (CO or CO/H$_2$) pressures. However, any convenient pressure can be used, and the product mixture is generally insensitive to pressure. Although CO or CO/H$_2$ pressures up about 200 atmospheres can be used, it is preferred to maintain the pressure within the range of about 3 to about 20 atmospheres.

The process of the invention can be performed over a broad temperature range. Generally, it is preferred to perform the process at a temperature within the range of about 20° C. to about 180°°C. A more preferred range is from about 90° C. to about 130° C. At temperatures greater than about 180° C., competing side reactions become important, while the reaction becomes too slow at temperatures below about 20° C.

The invention provides a way to make pyrrolidones under relatively mild temperature and pressure conditions. In addition, the process of the invention gives good yields of pyrrolidones compared with yields obtained in the absence of a pyridine promoter.

The following examples merely illustrate the invention. Those skilled in the art will recognize many variations that are within the spirit of the invention and scope of the claims.

EXAMPLES 1-7

General Procedure for Cyclocarbonylation

A 100-mL Hastelloy C pressure reactor equipped with a glass liner and a mechanical stirrer is charged with N-methylallylamine (26 mmol), Rh$_6$(CO)$_{16}$(0.050 mmol), pyridine promoter (29 mmol, see Table 1), and toluene (15 g). The reactor is sealed, and the headspace is purged for 15 min. with nitrogen. The reactor is pressurized with carbon monoxide (Examples 1-5) or CO/H$_2$ mixture (Examples 6-7) to 300 psi. The reaction mixture is then stirred and heated to 125° C., and is kept at 125° C. for 2 h. After cooling the mixture to 23° C., the gases are vented, and the liquid products are analyzed by gas chromatography. Results of the analyses appear in Table 1.

TABLE 1

Preparation of N-Methyl-2-pyrrolidone from N-Methylallylamine using Rh$_6$(CO)$_{16}$ and a Pyridine Promoter[1]

| Ex. # | Promoter | Conv. (%) | Selectivity (%)[2] NMP | EnAm | MDAA |
|---|---|---|---|---|---|
| C1* | None | 20˜ | 51 | 47 | 2 |
| 2 | 4-(dimethylamino)pyridine | 99 | 61 | 28 | 11 |
| 3 | 4-cyanopyridine | 60 | 47 | 2 | 50 |
| 4 | 4-methylpyridine | 72 | 50 | 2 | 48 |
| 5 | 3-(2-hydroxyethyl)pyridine | 70 | 48 | 41 | 11 |
| C6* | None[3] | 99 | 28 | 40 | 32 |
| 7 | 4-(dimethylamino)pyridine[3] | 94 | 55 | 16 | 29 |

[1]All reactions are performed in toluene at 125° C. for 2 hours.
[2]Selectivities measured by gas chromatography; NMP = N-methyl-2-pyrrolidone; EnAm = imine and enamine isomers of N-methylallylamine; MDAA = N-methyl-N,N-diallylamine; no pyridine by-products are detected.
[3]Reaction performed with 14% H$_2$ in the CO.
*Comparative examples The preceding examples are meant only as illustrations. The following claims define the scope of the invention.

We claim:

1. A cyclocarbonylation process for making a pyrrolidone, said process comprising reacting an allylic amine of the structure;

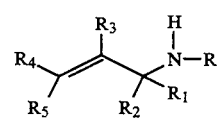

in which each of R, R$_1$, R$_2$, R$_3$, R$_4$, and R$_5$ separately represents hydrogen or a linear, branched, or cyclic C$_1$-C$_6$ alkyl, aryl, or aralkyl group; except that at least one of R$_1$ and R$_2$ is hydrogen, and at least one of R$_4$ and R$_5$ is hydrogen; with carbon monoxide in the presence of a rhodium carbonyl catalyst and a pyridine promoter to produce the pyrrolidone, wherein the promoter is used in an amount effective to enhance the yield of the pyrrolidone compared with the yield of pyrrolidone obtained in the absence of the promoter.

2. The process of claim 1 wherein the rhodium carbonyl catalyst is selected from the group consisting of rhodium carbonyls; rhodium compounds and rhodium carbonyl compounds that contain halides, nitrates, carboxylates, sulfonates, and amines; elemental forms of rhodium; rhodium compounds that contain complexed olefins; and polymer-bound rhodium.

3. The process of claim 1 wherein the rhodium carbonyl catalyst is $Rh_6(CO)_{16}$.

4. The process of claim 1 wherein the amount of rhodium carbonyl catalyst used is within the range of about $10^{-6}$ to about $10^{-1}$ moles of Rh per mole of allylic amine.

5. The process of claim 1 wherein the pyridine promoter is selected from the group consisting of pyridine, (dialkylamino)pyridines, alkylpyridines, arylpyridines, ortho-bipyridines, cyanopyridines, (2-hydroxyethyl)-pyridines, phenanthrolines, and (pyrrolidino)pyridines.

6. The process of claim 1 wherein the pyridine promoter is used in an amount within the range of about 0.5 moles to about 2 moles of pyridine promoter per mole of allylic amine.

7. The process of claim 1 performed at a CO or $CO/H_2$ pressure within the range of about 3 atmospheres to about 20 atmospheres.

8. A cyclocarbonylation process for making N-methyl-2-pyrrolidone, said process comprising reacting N-methylallylamine with carbon monoxide in the presence of a rhodium carbonyl catalyst and a pyridine promoter to produce N-methyl-2-pyrrolidone, wherein the promoter is used in an amount effective to enhance the yield of the N-methyl-2-pyrrolidone compared with the yield of N-methyl-2-pyrrolidone obtained in the absence of the promoter.

9. The process of claim 8 wherein the rhodium carbonyl catalyst is selected from the group consisting of rhodium carbonyls; rhodium compounds and rhodium carbonyl compounds that contain halides, nitrates, carboxylates, sulfonates, and amines; elemental forms of rhodium; rhodium compounds that contain complexed olefins; and polymer-bound rhodium.

10. The process of claim 8 wherein the rhodium carbonyl catalyst is $Rh_6(CO)_{16}$.

11. The process of claim 8 wherein the amount of rhodium carbonyl catalyst used is within the range of about $10^{-6}$ to about $10^{-4}$ moles of Rh per mole of N-methylallylamine.

12. The process of claim 8 wherein the pyridine promoter is selected from the group consisting of pyridine, (dialkylamino)pyridines, alkylpyridines, arylpyridines, ortho-bipyridines, cyanopyridines, (2-hydroxyethyl)-pyridines, phenanthrolines, and (pyrrolidino)pyridines.

13. The process of claim 8 wherein the pyridine promoter is used in an amount within the range of about 0.5 moles to about 2 moles of pyridine promoter per mole of N-methylallylamine.

14. The process of claim 8 performed at a CO or $CO/H_2$ pressure within the range of about 3 atmospheres to about 20 atmospheres.

15. A cyclocarbonylation process for making N-methyl-2-pyrrolidone, said process comprising reacting N-methylallylamine with carbon monoxide at a pressure within the range of about 3 to about 20 atmospheres in the presence of $Rh_6(CO)_{16}$ and a pyridine promoter selected from the group consisting of pyridine and (dialkylamino)pyridines to produce N-methyl-2-pyrrolidone, wherein the promoter is used in an amount effective to enhance the yield of the N-methyl-2-pyrrolidone compared with the yield of N-methyl-2-pyrrolidone obtained in the absence of the promoter.

16. The process of claim 15 wherein the $Rh_6(CO)_{16}$ catalyst is used in an amount within the range of about $10^{-5}$ to about $10^{-2}$ moles of Rh per mole of N-methylallylamine.

17. The process of claim 15 wherein the pyridine promoter is used in an amount within the range of about 0.5 moles to about 2 moles of pyridine promoter per mole of N-methylallylamine.

18. The process of claim 15 wherein the pyridine promoter is 4-(dimethylamino)pyridine.

* * * * *